US011932892B2

(12) United States Patent
Ibrahim

(10) Patent No.: US 11,932,892 B2
(45) Date of Patent: Mar. 19, 2024

(54) PROCESS FOR PRODUCTION OF KERATIN MICROFIBERS AND PROTEIN HYDROLYSATE FROM POULTRY FEATHERS VIA MICROBIAL HYDROLYSIS

(71) Applicant: Bioextrax AB, Lund (SE)

(72) Inventor: Mohammad H. A. Ibrahim, Veberöd (SE)

(73) Assignee: Bioextrax AB, Lund (SE)

( * ) Notice: Subject to any disclaimer, the term of this patent is extended or adjusted under 35 U.S.C. 154(b) by 525 days.

(21) Appl. No.: 17/283,575

(22) PCT Filed: Oct. 17, 2019

(86) PCT No.: PCT/EP2019/078189
§ 371 (c)(1),
(2) Date: Apr. 8, 2021

(87) PCT Pub. No.: WO2020/079133
PCT Pub. Date: Apr. 23, 2020

(65) Prior Publication Data
US 2021/0340587 A1 Nov. 4, 2021

(30) Foreign Application Priority Data
Oct. 17, 2018 (EP) ..................................... 18200976

(51) Int. Cl.
C12P 21/06 (2006.01)
C07K 14/78 (2006.01)
(52) U.S. Cl.
CPC .............. *C12P 21/06* (2013.01); *C07K 14/78* (2013.01)

(58) Field of Classification Search
CPC ....................................................... C12P 21/06
See application file for complete search history.

(56) References Cited

U.S. PATENT DOCUMENTS

| | | |
|---|---|---|
| 4,959,311 A | 9/1990 | Shih et al. |
| 5,705,030 A | 1/1998 | Gassner, III et al. |
| 8,182,551 B1 | 5/2012 | Meyerhoeffer, Jr. et al. |
| 9,068,167 B2 * | 6/2015 | Kamp ........................ A61P 9/00 |
| 9,695,455 B2 * | 7/2017 | Eslahi ................... A61K 9/5169 |
| 10,945,940 B2 * | 3/2021 | Lee ......................... A61Q 19/08 |
| 2010/0196302 A1 | 8/2010 | Vermelho et al. |

(Continued)

FOREIGN PATENT DOCUMENTS

| | | |
|---|---|---|
| EP | 1985647 A1 | 10/2008 |
| WO | 1989/09278 A1 | 10/1989 |

(Continued)

OTHER PUBLICATIONS

Aranberri, I., et al., Fully biodegradable biocomposites with high chicken feather content, Polymers 2017, 9(11), 593; https://doi.org/10.3390/polym9110593.

(Continued)

*Primary Examiner* — Andrew T Piziali
(74) *Attorney, Agent, or Firm* — Weston R. Gould; Dinsmore & Shohl LLP

(57) ABSTRACT

The present invention relates to a process of converting feather materials into keratin-rich microfibers and soluble protein hydrolysate, the process comprising using a microbial hydrolysis technique.

16 Claims, 7 Drawing Sheets

(56) References Cited

U.S. PATENT DOCUMENTS

| | | | |
|---|---|---|---|
| 2013/0091912 A1* | 4/2013 | Puah | C02F 3/34 |
| | | | 435/252.4 |
| 2015/0197783 A1* | 7/2015 | Yu | A23K 50/40 |
| | | | 435/68.1 |
| 2015/0208694 A1* | 7/2015 | Yu | C07K 14/465 |
| | | | 426/657 |
| 2016/0265020 A1 | 9/2016 | Eslahi et al. | |
| 2017/0224540 A1 | 8/2017 | Li et al. | |
| 2018/0263259 A1* | 9/2018 | Gade | C12P 21/06 |

FOREIGN PATENT DOCUMENTS

| | | |
|---|---|---|
| WO | 2007/023199 A1 | 3/2007 |
| WO | 2015/028701 A1 | 3/2015 |
| WO | 2017/221015 A1 | 12/2017 |

OTHER PUBLICATIONS

Büyükkaya, K., Effects of the Fiber Diameter on Mechanic Properties in Polymethyl-Methacrylate Composites Reinforced with Goose Feather Fiber, 2017 Mater. Sci. Appl. 8, 811-827, https://doi.org/10.4236/msa.2017.811059.

El-Refai, H., et al., Improvement of the newly isolated Bacillus pumilus FH9 keratinolytic activity, Process Biochemistry, Elsevier Ltd, GB, 40(7): 2325-2332, XP027794153, ISSN: 1359-5113, Jun. 2005.

Karthikeyan, R., et al., Industrial applications of keratins—A review, Journal of Scientific & Industrial Research. 66: 710-715, Sep. 2017.

Manginsay, G., et al., Chicken Feathers as Substitute for Fine Aggregates in Concrete, Mindanao J. Sci. Technol., 13: 109-131, 2015.

Molins, G., et al., Chicken feathers based composites: A Life Cycle Assessment, 15th Eur. Conf. Compos. Mater. Jun. 24-28, 2012.

Muthusamy, G., et al., Response surface methodology based optimization of keratinase production from alkali-treated feather waste and horn waste using Bacillussp. MG-MASC-BT, Journal of Industrial and Engineering Chemistry, The Korean Society of Industrial and Engineering Chemistry, KR, 27: 25-30, XP0329611560, ISSN: 1226-086X, Dec. 30, 2014.

Nagal, S., et al., Feather degradation by strains of Bacillus isolated from decomposing feathers, Brazilian Journal of Microbiology 41: 196-200, ISSN 1517-8382, 2010.

Papadopoulos, M., Processed chicken feathers as feedstuff for poultry and swine. A review, Agric. Wastes 14(4): 275-290. https://doi.org/10.1016/S0141-4607(85)80009-3, 1985.

Queiroga, A., et al., Potential use of wool-associated *Bacillus* species for biodegradation of keratinous materials, International Biodeterioration & Biodegradation, 70: 60-65, May 2012.

Reddy, N., Non-food industrial applications of poultry feathers, Waste Management, 45: 91-107, XP055575458, US, ISSN: 0956-053X, DOI: 10.1016/j.wasman.2015.05.023, Nov. 2015.

Sinkiewicz, I., et al., Alternative Methods of Preparation of Soluble Keratin from Chicken Feathers, Waste and Biomass Valorization. 8: 1043-1048. https://doi.org/10.1007/s12649-016-9678-y, 2017.

Stettenheim, P., The Integumentary Morphology of Modern Birds—An Overview, Amer. Zool. 40: 461-477. 2000.

Suntornsuk, W., et al., Feather degradation by *Bacillus* sp. FK 46 in submerged cultivation, Bioresource Technology, 86: 239-243, XP055574996, 2003.

Supri, A., et al., Chicken feather fibers-recycled high-density polyethylene composites: The effect of $\epsilon$-caprolactam, J. Thermoplast. Compos. Mater., 28(3): 327-339. 2013, https://doi.org/10.1177/0892705713484746.

Tesfaye, T., et al., Valorisation of chicken feathers: a review on recycling and recovery route-current status and future prospects, Clean Technol. Environ. Policy, 19(10): 2363-2378, 2017, https://doi.org/10.1007/s10098-017-1443-9.

Wrzesniewska-Tosik, K., et al., Fibrous composites based on keratin from chicken feathers, Fibres and Text. East. Eur., 19(6): 118-123. 2011.

Yusuf, I., et al., Keratinase production and biodegradation of polluted secondary chicken feather wastes by a newly isolated multi heavy metal tolerant bacterium—*Alcaligenes* sp. AQ05-001, Journal of Environmental Management, 183: 182-195, XP055574985, Amsterdam, NL, ISSN: 0301-4797, DOI: 10.1016/j.jenvman.2016. 08.059, Dec. 2016.

Abdel-Naby, M. et al.., Structural characterization, catalytic, kinetic and thermodynamic properties of Keratinase from Bacillus pumilus FH9, Int. Journal of Biological Macromolecules, 105: 973-980, Jul. 23, 2017.

Villa, A. et al., Feather keratin hydrolysates obtained from microbial keratinases: effect on hair fiber, MMC Biotechnology, 13(15): pp. 1-11, Feb. 18, 2013.

\* cited by examiner

PROCESS FOR PRODUCTION OF KERATIN MICROFIBERS AND PROTEIN HYDROLYSATE FROM POULTRY FEATHERS VIA MICROBIAL HYDROLYSIS

CROSS REFERENCE TO RELATED APPLICATIONS

This application is a U.S. National Stage of international application PCT/EP2019/078189 filed Oct. 17, 2019, which claims priority to European Application No: 18200976.1 filed Oct. 17, 2018, the entire contents of each of which are incorporated herein by reference.

TECHNICAL FIELD

The present invention relates to a process of converting feather materials into keratin-rich microfibers and soluble protein hydrolysate, the process comprising using a microbial hydrolysis technique.

BACKGROUND

In the last decades, the global interest in designing and manufacturing new materials from renewable resources has increased. Both the industry and the society are looking for materials that can replace conventional oil-based materials while being more environmentally benign. A recent trend is to develop solutions that enable a shift from linear to circular economy, in which waste can be used as a resource with resultant economic and environmental benefits. One such example is to utilize the globally abundant waste feathers from chicken industry, about 5 million ton per year, as a cheap and renewable source of fibers for reinforcement of materials (Aranberri et al., 2017; Wrześniewska-Tosik et al., 2011). The unique physical and chemical structure of poultry feathers makes it not only interesting from a materials perspective, but also as a rich protein source for oligopeptides and amino acids for feed applications (90% of feather dry weight is β-keratin) (Tesfaye et al., 2017). Utilization of waste poultry feathers will have high environmental and economic impact in comparison to burning or landfilling (Sinkiewicz et al., 2017).

Feather fibers can be used to make insulation materials, biosorbents, membranes, cell-scaffolds, among other things. These fibers have the potential to enhance the biodegradability, elasticity, hydrophobicity and density of reinforced composites showing a wide spectrum of material applications in construction, medicine, cosmetics and agriculture. (Tesfaye et al., 2017; Reddy, 2015)

In green building applications, raw intact feathers are used as cheap renewable material to enhance concrete density and mechanical properties. (Manginsay, G. P., Guinita-Cabahug, R., 2015) Several mechanical methods are designed to prepare fine fibers from poultry feathers, (Meyerhoeffer and Showalter, 2002; Graeter, 1998) however the large and varied size ranges and the low mass recovery of fine fibers is a barrier to a cost-efficient process. (Tesfaye et al., 2017)

Feather reinforced materials usually show improved mechanical properties; however, the concentration and size of fibers affect the interfacial adhesion between the fibers and the material phases. (Supri et al., 2015; Büyükkaya, 2017)

Recently, micro/nanofibers from different kind of proteins have gained much interest, however the electrospinning methods usually used for making them cannot be applied except after chemical solubilisation of the keratin structure. This technology is both expensive and difficult to upscale for bulk material production besides having negative environmental impacts. (Molins et al., 2012)

The thermo-chemical keratin-hydrolyzing methods are also used for feed applications of feather wastes. The low nutritional value of the produced hydrolysate "feather meal", however, decreases the industrial interest of these methods. (Papadopoulos, 1985)

Most fibers-applications, and in particular the production of fiber-reinforced materials such as wood or plastic composite, require the fibers to be in the micro-size range. It has so far been challenging to obtain microfibers from feather material with a high yield, and this problem has strongly limited their use in the industry.

The process presented here is a gentle biobased technique for production of keratin microfibrous structures and water-soluble keratin oligopeptides and amino acids.

SUMMARY

The present invention is directed to keratin-rich microfibers deriving from poultry feather material. The keratin-rich microfibers of the present disclosure are particularly advantageous over previously disclosed microfibers because of their size. In fact, the inventors have found that by simply hydrolyzing wet feather material with the bacteria $B.\ pumilus$, keratin-rich microfibers having a length of between 20 and 200 μm are obtained. The process presented here is a gentle biobased technique in which the growth of a microbial strain $B.\ pumilus$ partially hydrolyses poultry feather to its microfibrous structure. In addition, the process also releases a portion of water-soluble keratin oligopeptides and amino acids, which can be used to produce feed material and/or fertilizers.

One aspect of the present disclosure is directed to a microfiber composition comprising keratin microfibers, wherein said keratin microfibers comprise at least 75% dry weight keratin, and wherein said keratin microfibers have a length of between 20 μm and 200 μm and a diameter of between 1 μm and 10 μm, and wherein said keratin microfibers comprise hollow cylindrical structures.

One aspect of the present disclosure is directed to a microfiber composition comprising keratin-rich microfibers, wherein said keratin-rich microfibers comprise at least 75% dry weight keratin, and wherein said microfibers have a length of between 20 μm and 200 μm.

Another aspect of the present disclosure is directed to a process for production of keratin microfibers from feather material, the process comprising:
  a) Providing a fermentation medium;
  b) Providing feather material at a concentration of at least 25 grams dry weight/L of fermentation medium;
  c) Providing a keratin-degrading bacteria;
  d) Contacting the fermentation medium, the feather material and the keratin-degrading bacteria, and thereby fermenting the feather material to obtain a fermented composition;
  e) Separating the fermented composition obtained in step d) into one supernatant fraction and one precipitate fraction, wherein the precipitate fraction obtained in the separation step comprises keratin microfibers, thereby obtaining keratin microfibers, wherein said keratin microfibers comprise at least 75% dry weight keratin, and wherein said microfibers have a length of between 20 μm and 200 μm.

One aspect of the present disclosure is directed to a keratin microfiber composition obtained by the process of the present disclosure.

Another aspect of the present disclosure is directed to a process for production of microfibers from feather material, the process comprising:
a) Providing feather material; and
b) Fermenting the feather material to obtain a composition comprising microfibers.

A further aspect of the present disclosure is directed to a process for production of a protein hydrolysate, wherein the process comprises
a. Providing feather material; and
b. Fermenting the feather material to obtain a composition comprising a protein hydrolysate.

In one further aspect, the present disclosure relates to a composition comprising a protein hydrolysate obtainable by the process disclosed herein.

Further, one aspect of the present disclosure relates to a use of the composition disclosed herein as a feed product.

In one other aspect, the present disclosure relates to a use of the microfiber composition disclosed herein, and/or obtainable by the process disclosed herein, for manufacture of a composite material.

A further aspect of the present disclosure is directed to a system for extraction of microfibers from feather material, comprising a fermenting reactor, said system arranged for performing the process of production of microfibers disclosed herein.

An even further aspect of the present disclosure is directed to a kit of parts for extracting microfibers, comprising a bacterial strain *Bacillus pumilus* FH9, and instructions for use.

DETAILED DESCRIPTION

Keratin-Rich Microfibers

Figure 1:
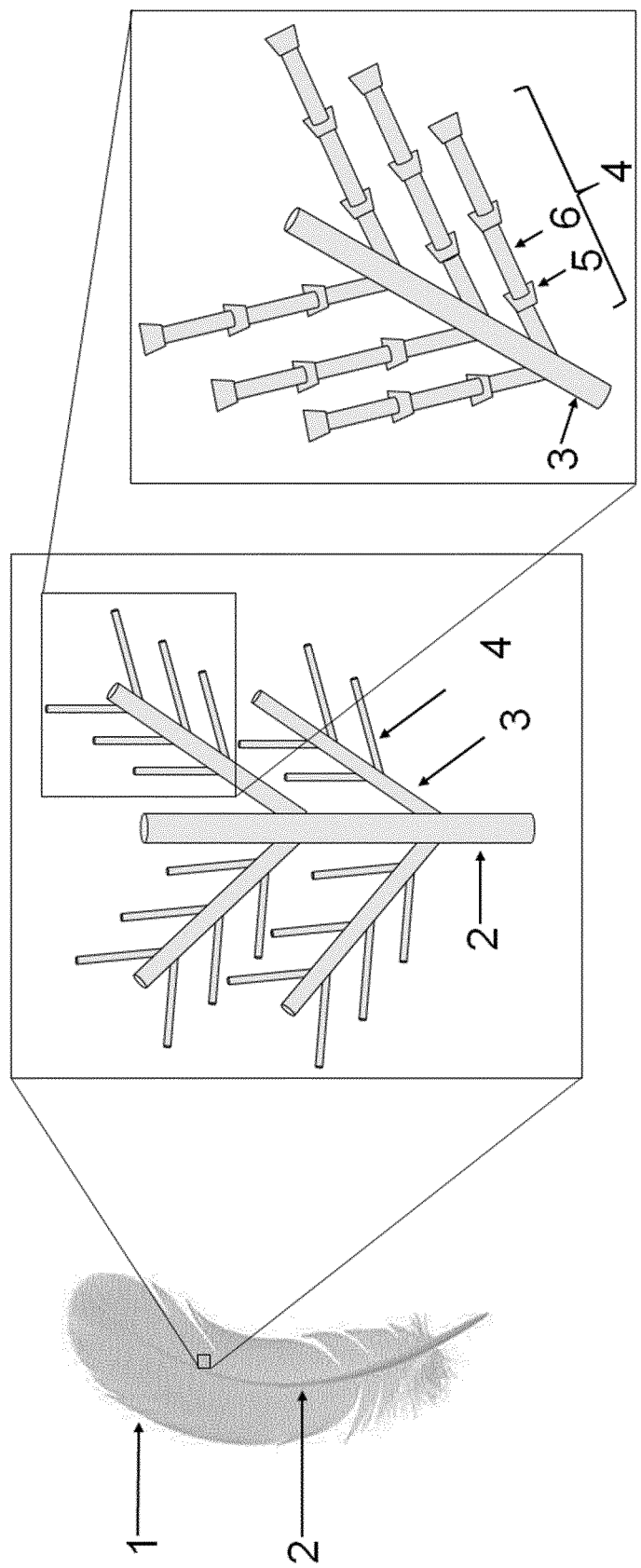
FIG. 1: The physical structure of a feather: macro- and microstructures of a bird feather are shown (general example, with magnified graphs explaining the microscopic parts. (Modified from Stettenheim 2000) Legend: 1: vane; 2: rachis; 3: barb; 4: barbule; 5: hooklet (node); 6: internode.
Figure 2:
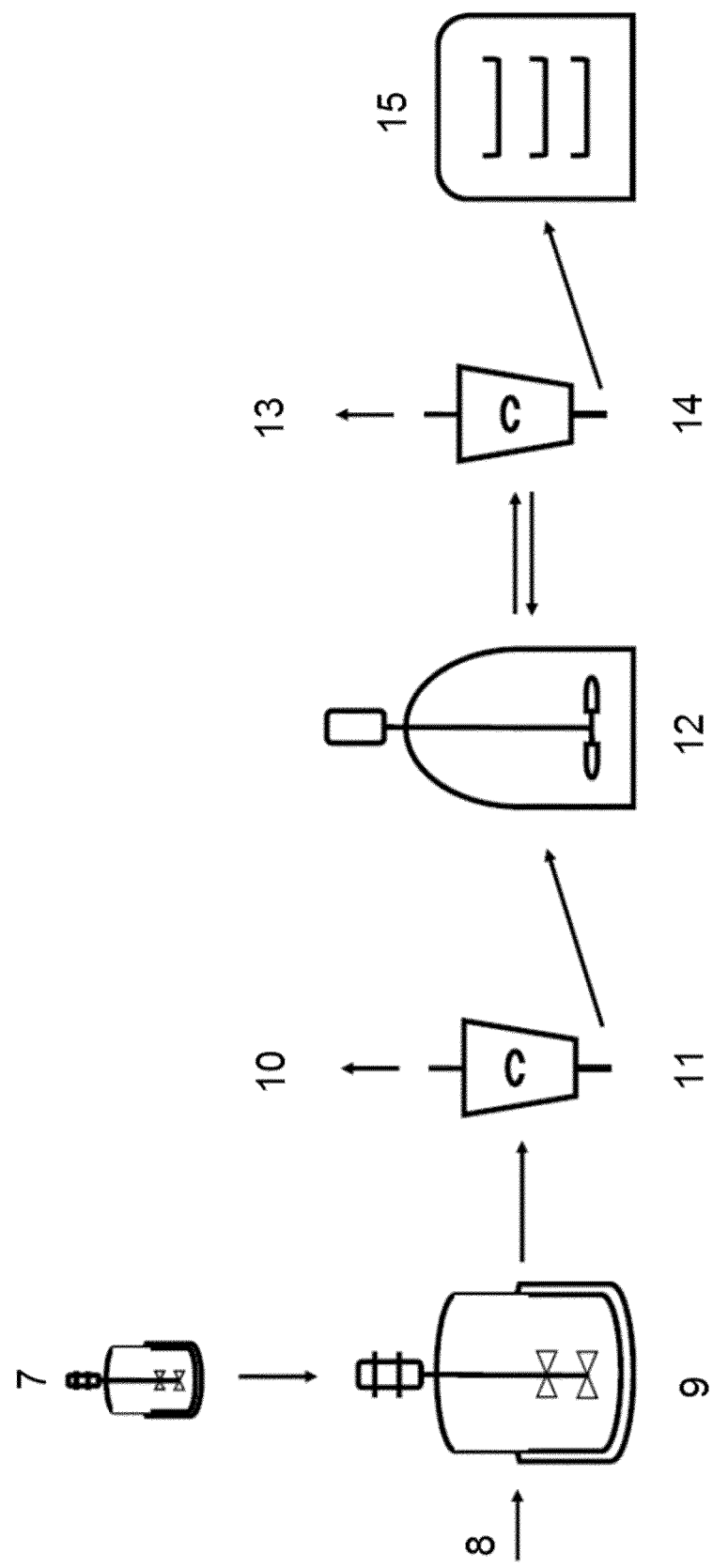
FIG. 2: Flow diagram of feather hydrolysis process for obtaining pure microfibers and protein hydrolysate:
A) Seed culture grown for 12-18 h in basal medium
B) Feather fermentative hydrolysis 24-80 h (24 h). Dry feather concentration of 50-60 g/L
C) Separation of soluble keratin hydrolysate at high speed centrifugation or microfiltration
D) Washing of fibers in water with mixing at room temperature for 10-30 minutes
E) Separation of fibers away from cells via low speed centrifugation or microfiltration
F) Repeated washing and separation of recovered microfibers in steps D) and E).
G) Recovery of cells and their use as plant/soil fertilizer
H) Drying of recovered pure microfibers.
Legend: 7: seed culture; 8: wet feather; 9: hydrolysis; 10: soluble hydrolysate; 11: crude microfibers; 12: mixing and washing; 13: bacterial cells; 14: pure microfibers; 15: drying.

One aspect of the present disclosure is directed to a microfiber composition comprising keratin microfibers, wherein said keratin microfibers comprise at least 75% dry weight keratin, and wherein said keratin microfibers have a length of between 20 μm and 200 μm and a diameter of between 1 μm and 10 μm, and wherein said keratin microfibers comprise hollow cylindrical structures.

One aspect of the present disclosure is directed to a microfiber composition comprising keratin-rich microfibers, wherein said keratin-rich microfibers comprise at least 75% dry weight keratin, and wherein said microfibers have a length of between 20 μm and 200 μm.

In one further aspect, the present disclosure relates to a composition comprising microfibers obtainable by the process disclosed herein.

The terms "keratin-rich microfiber" and "keratin microfiber" as used herein are used to refer to microfibers comprising at 75% keratin, and comprising hollow cylindrical structures typical of feathers.

The size and composition of the keratin microfibers of the present disclosure, together with their three-dimensional (3D) structure comprising hollow cylindrical structures typical of feathers, ensures that the microfibers disclosed herein have low density and low weight, in particular lower density and lower weight compared to keratin particles obtained by mechanical and chemical process, such as processes that comprise dissolution of feather material, precipitation of the dissolved feather material and re-polymerization of the precipitated feather material. Hence, the microfibers of the present disclosure are the ideal ingredient for manufacture of composite materials, such as wood composites and plastic composites. Due to their size and composition the keratin-rich microfibers of the present disclosure easily blend with most polymers used to manufacture plastic, allow easy production of fiber-reinforced plastic.

The size of the microfibers of the present disclosure is also advantageous when the microfibers are used in composite materials. Microfibers of this size range give more elasticity compared to longer fibers and particles.

In one embodiment, the microfiber composition disclosed herein comprises keratin-rich microfibers comprising at least 75% dry weight keratin.

In one embodiment, the microfiber composition disclosed herein comprises keratin-rich microfibers comprising between 75% dry weight keratin and 100% dry weight keratin, such as between 80% dry weight keratin and 100% dry weight keratin, such as between 85% dry weight keratin and 100% dry weight keratin, such as between 75% dry weight keratin and 90% dry weight keratin.

In one embodiment, the microfiber composition disclosed herein comprises keratin-rich microfibers comprising about 90% dry weight keratin.

In one embodiment, the microfiber composition disclosed herein comprises keratin-rich microfibers having a length of between 20 µm and 200 µm, such as a length of between 25 µm and 200 µm, such as of between 30 µm and 200 µm, such as of between 35 µm and 200 µm, such as of between 40 µm and 200 µm, such as of between 50 µm and 200 µm, such as of between 60 µm and 200 µm, such as of between 70 µm and 200 µm, such as of between 80 µm and 200 µm, such as of between 90 µm and 200 µm, such as of between 100 µm and 200 µm, such as of between 20 µm and 180 µm, such as of between 20 µm and 150 µm, such as of between 20 µm and 120 µm, such as of between 20 µm and 100 µm, such as of between 20 µm and 90 µm, such as of between 20 µm and 80 µm, such as of between 20 µm and 70 µm, such as of between 20 µm and 60 µm, such as of between 30 µm and 150 µm.

In one embodiment, the microfiber composition disclosed herein comprises keratin-rich microfibers having a length of between 30 µm and 150 µm.

In one embodiment, the microfiber composition disclosed herein comprises keratin-rich microfibers having a length of at least 20 µm, such as a length of at least 25 µm, such as a length of at least 30 µm, such as a length of at least 35 µm, such as a length of at least 40 µm, such as a length of at least 50 µm, such as a length of at least 60 µm, such as a length of at least 70 µm, such as a length of at least 80 µm, such as a length of at least 90 µm, such as a length of at least 100 µm.

In one embodiment, the microfiber composition disclosed herein comprises keratin-rich microfibers having a length of at the most 60 µm, such as a length of at the most 70 µm, such as a length of at the most 80 µm, such as a length of at the most 90 µm, such as a length of at the most 100 µm, such as a length of at the most 120 µm, such as a length of at the most 150 µm, such as a length of at the most 180 µm, such as a length of at the most 200 µm.

In one embodiment, the microfiber composition disclosed herein comprises keratin-rich microfibers having a diameter or width of between 1 µm and 10 µm, such as of between 1 µm and 6 µm, such as of between 2 µm and 6 µm, such as of between 3 µm and 6 µm, such as of between 4 µm and 6 µm, such as of between 5 µm and 6 µm, such as of between 1 µm and 5 µm, such as of between 1 µm and 4 µm, such as of between 1 µm and 3 µm, such as of between 1 µm and 2 µm.

In one embodiment, the microfiber composition disclosed herein comprises keratin-rich microfibers having a diameter or width of between 2 µm and 6 µm.

In one embodiment, the microfiber composition disclosed herein comprises keratin-rich microfibers having a diameter or width of about 1 µm, such as a diameter or width of about 2 µm, such as a diameter or width of about 3 µm, such as a diameter or width of about 4 µm, such as a diameter or width of about 5 µm, such as a diameter or width of about 6 µm, such as a diameter or width of about 7 µm, such as a diameter or width of about 8 µm.

In one embodiment, the microfiber composition disclosed herein comprises keratin microfibers, which are insoluble in an aqueous solution. This is due to the process used for manufacturing the microfibers, as well as to their structural features. This is of advantage for most uses of said microfiber composition and in particular for use of the microfiber composition in composite materials, as stability at high humidity and in aqueous conditions is often desirable.

In one embodiment, the microfiber composition disclosed herein comprises keratin microfibers, which have low or no water solubility.

In one embodiment, the microfiber composition disclosed herein comprises keratin microfibers, which are stable in aqueous conditions, such as in presence of high humidity.

Methods for measuring length and diameter of microfibers are known in the art. For example the diameters and lengths of the fibers can be estimated by observing a sample of the obtained crude microfibers or purified microfibers under a transmission electron microscope (TEM). Other methods and instruments exist to determine or estimate fibers length and diameter, for example nanoparticles size can be measured by dynamic light scattering using a Zetasizer Nano-Z (Malvern Instruments). Even further methods to determine or estimate fibers length and diameter exist and they are known to the person of skills in the art.

In one embodiment, the microfiber composition disclosed herein comprises keratin-rich microfibers comprising hollow cylindrical structures.

In fact, the keratin-rich microfibers of the present disclosure are obtained from poultry feather material, which is characterized by hollow cylindrical structures of various diameters, mostly of diameter or width of between 1 µm and 10 µm. These structures are commonly referred to as barbs and barbules (see FIG. 1). In particular, barbules are attached to a barb, and the distance between adjacent barbules is of between 20 µm and 50 µm, often of about 30 µm. The barbules are characterized by having smaller fibers, called internodes, attached together with hooklets (nodes). The average distance between adjacent hooklets on a barbule is of between 20 µm and 50 µm. The keratin-rich microfibers of the present disclosure comprise fragments of barbs and barbules, wherein each of said fragments comprises between one and six internodes.

In one embodiment, the microfiber composition disclosed herein comprises keratin-rich microfibers comprising at least one internode and at the most six internodes, such as at least one internode and at the most five internodes.

In one embodiment, the microfiber composition disclosed herein comprises keratin-rich microfibers comprising between 75% dry weight proteins and 100% dry weight proteins, such as between 80% dry weight proteins and 100% dry weight proteins, such as between 85% dry weight proteins and 100% dry weight proteins, such as between 75% dry weight keratin and 95% dry weight keratin, such as between 80% dry weight keratin and 95% dry weight keratin, such as between 85% dry weight keratin and 95% dry weight keratin.

In one embodiment, the microfiber composition according to the present disclosure comprises keratin-rich microfibers comprising protein, in the amounts described herein, water and lipids.

In one embodiment, the microfiber composition according to the present disclosure, comprises keratin-rich microfibers comprising between 0.1% dry weight lipids and 2% dry weight lipids, such as about 1% dry weight lipids.

In one embodiment, the microfiber composition disclosed herein is the product of the process disclosed herein.

Hydrolysis of the Feather Material

The present disclosure relates to keratin-rich microfibers and to a process for production of said keratin-rich microfibers using bacterial hydrolysis. The present inventors have found that a single fermentation step, wherein the fermentation is conducted with help of keratin-degrading bacteria, is sufficient for hydrolysing feather material and so obtaining keratin-rich microfibers. Then, it suffices to apply a simple separation method to divide the fermented composition into a precipitate, comprising crude microfibers, and a supernatant, comprising a protein hydrolysate. The inventors have optimized the fermentation conditions and found that an initial concentration of feather material of at least 25 grams dry weight/L of fermentation medium, preferably of 40-60 g/L, is needed for directing the hydrolysis towards production of keratin microfibers rather than an amino acids-rich hydrolysate. The disclosed process results in transforming the initial feather material into about 50 to 90% dry weight microfibers and 10 to 50% protein hydrolysate, Moreover, between 1 and 11% dry weight of the initial feather material is not converted.

In some embodiments, the feather material is provided at a concentration of 30 g dry weight/L or above, such as of 35 g dry weight/L or above, such as of 40 g dry weight/L or above, such as of 50 g dry weight/L or above, such as of 40 to 60 g dry weight/L of fermentation medium.

In some embodiments, the feather material is the sole source of carbon and/or nitrogen for the keratin-degrading bacteria.

In some embodiments, the provided fermentation medium is free from carbon and/or nitrogen sources. Thus, the feather material is the only available carbon and/or nitrogen source for the keratin-degrading bacteria.

The feather material will stimulate the keratin-degrading bacteria to produce the necessary enzymes to hydrolyse feathers to microfibers.

In some embodiments, the process disclosed herein converts the initial feather material into about 50% dry weight crude microfibers and about 45% protein hydrolysate, such as into about 55% dry weight crude microfibers and about 40% protein hydrolysate, such as into about 60% dry weight crude microfibers and about 35% protein hydrolysate, such as into about 65% dry weight crude microfibers and about 30% protein hydrolysate, such as into about 70% dry weight crude microfibers and about 25% protein hydrolysate, such as into about 80% dry weight crude microfibers and about 15% protein hydrolysate, wherein 1 to 11% dry weight of the initial feather material is not converted.

However, if the conditions of the process disclosed herein are changes substantially, the outcome of the process may differ and a different ratio of microfiber to protein hydrolysate may be obtained. For example, starting with an initial concentration of feather material below 25 grams dry weight/L fermentation medium, preferably of 20 grams dry weight/L or less, the feather material is hydrolysed to a large extent to proteins and/or amino acids, instead of to microfibers, meaning that a complete hydrolysis of the feather material may occur.

One aspect of the present disclosure is directed to a process for production of keratin microfibers from feather material, the process comprising:
 a) Providing a fermentation medium;
 b) Providing feather material at a concentration of at least 25 grams dry weight/L of fermentation medium;
 c) Providing a keratin-degrading bacteria;
 d) Contacting the fermentation medium, the feather material and the keratin-degrading bacteria, and thereby fermenting the feather material to obtain a fermented composition;
 e) Separating the fermented composition obtained in step d) into one supernatant fraction and one precipitate fraction, wherein the precipitate fraction obtained in the separation step comprises keratin microfibers, thereby obtaining keratin microfibers, wherein said keratin microfibers comprise at least 75% dry weight keratin, and wherein said microfibers have a length of between 20 µm and 200 µm.

Hence, another aspect of the present disclosure is directed to a process for production of keratin-rich microfibers from feather material, the process comprising:
 a) Providing feather material; and
 b) Fermenting the feather material to obtain a composition comprising microfibers.

The keratin rich microfibers obtained by the disclosed process are described in detail in the section above "Keratin-rich microfibers".

In one embodiment, the microfibers obtained by the process according to the present disclosure are keratin-rich microfibers.

The fermented composition comprises microfibers as well as protein hydrolysate and fermenting cells. Hence, it is beneficial to separate the microfibers from the remaining part of the composition. In one embodiment, the process of the present disclosure further comprises a separation step. For example, said separation step may comprise centrifugation and/or filtration. For example, high speed centrifugation may be applied once or more times. An alternative to centrifugation is filtration. Microfiltration may be suitable for separating the obtained keratin-rich microfibers from the remaining part of the fermented composition in only one step or only few steps. Hence, in one embodiment of the present disclosure, the separation step is conducted after the fermenting step.

The separation step of the process of the present disclosure will result in one supernatant fraction and one precipitate fraction. The precipitate fraction obtained in the separation step disclosed herein comprises microfibers, such as crude microfibers. In some embodiments, depending on the separation method used, the precipitate fraction obtained in the separation step disclosed herein further comprises fermenting cells.

The crude microfibers obtained after the separation step can be used without any further purification, for example for production of composite materials to be used as construction materials. The crude microfibers can for example be used without any further purification for production of wood composites, plastic composites and homocomposites.

However, some applications of the keratin-rich microfibers of the present disclosure may require a high degree of purity. Hence, in one embodiment, the process of the present disclosure further comprises a step of purifying the precipitate fraction, such as the crude microfibers.

Purification of the crude microfibers can easily be obtained by applying one or more cycles of separation, for example one or more centrifugation steps, or one or more filtration steps, or a combination of one or more centrifugation steps with one or more filtration steps.

In one embodiment, the purification step according to the process of the present disclosure comprises re-suspending the precipitate fraction. For example, the crude microfibers can be re-suspended in water or in another suitable liquid solution.

In one embodiment, the purification step according to the process of the present disclosure comprises washing the precipitate fraction and/or mixing the precipitate fraction with water or in another suitable liquid solution. For example, the crude microfibers can be mixed with water or in another suitable liquid solution and washed so that it is well re-suspended.

In one embodiment, the purification step according to the process of the present disclosure comprises a. re-suspending the precipitate fraction, and/or washing the precipitate fraction and/or mixing the precipitate fraction with water; b. centrifugation and/or filtration of the re-suspended, washed and/or mixed precipitate fraction.

In one embodiment, the purification step according to the process of the present disclosure comprises centrifugation and/or filtration of the re-suspended, washed and/or mixed precipitate fraction. If centrifugation is used, different centrifugation steps at different speed may be beneficially applied so that the keratin-rich microfibers are separated from fermenting cells and soluble material.

In one embodiment, the purification step according to the process of the present disclosure results in one supernatant fraction and one precipitate fraction. The precipitate fraction obtained in the purification step according to the process of the present disclosure comprises purified keratin microfibers. The supernatant fraction obtained in the purification step according to the process of the present disclosure comprises fermenting cells.

In one embodiment, the purification step according to the process of the present disclosure is optionally repeated on the precipitate fraction, which comprises first crude microfibers and then purified microfibers, at least twice, such as at least three or more times, or until the desired degree of purity of the microfibers is obtained.

The supernatant fraction obtained after the first purification step comprises fermenting cells. The supernatant fraction may so be recycled to the fermenter or the seed culture reactor, so that the fermenting cells are re-used in the following fermentations. For example, the supernatant fraction may be recycled to the fermenter and so there would be no need for a seed culture reactor. The supernatant fraction obtained after the first purification step may comprise fermenting cells in a large amount of water and it may be beneficial to remove said water prior to re-using the cells for fermentation.

The precipitate fraction obtained in the purification step according to the process of the present disclosure comprises purified microfibers and may also comprise water. Depending on the intended application, it can be desirable to remove any residual water from the precipitate fraction comprising microfibers. Similarly, also the crude microfibers obtained from the separation step may comprise residual water, which may be beneficially removed.

Hence, in one embodiment, the process of the present disclosure further comprises a step of drying the precipitate fraction obtained from the separation step and/or from the purification step. In one embodiment, the process of the present disclosure further comprises a step of drying the supernatant fraction obtained from the separation step and/or from the purification step.

The drying step should be conducted with care and at conditions that are not damaging for the keratin-rich microfibers and/or for the fermenting cells. The person of skills in the art knows which drying methods are available and is able to choose an appropriate method based on common knowledge.

The supernatant fraction obtained in the separation step according to the process of the present disclosure comprises a protein hydrolysate. For example, the protein hydrolysate may comprise soluble proteins, amino acids and/or oligopeptides. The obtained protein hydrolysate is a side product of the disclosed process; however, the protein hydrolysate is also a valuable product. The protein hydrolysate obtained after the separation step may also comprise fermenting cells and can be used in several ways, for example, it can be recirculated to the fermenting reactor bringing proteins and amino acid that are useful in the fermentation. The protein hydrolysate can also be further processed into a feed product or into a soil or plant fertilizer.

Hence, in one embodiment, the process according to the present disclosure further comprises a step of processing the obtained protein hydrolysate into a feed product and/or into a plant or soil fertilizer.

Feather Material

The present disclosure relates to using feather material for production of keratin microfibers, such as keratin-rich microfibers and, optionally, a protein hydrolysate.

In one embodiment of the present disclosure, the feather material comprises quill and/or vane of feathers. In fact, the process of the present disclosure is capable of hydrolysing to microfibers both the vane part and the quill part of feathers.

In one embodiment of the present disclosure, the feather material fed to the disclosed process comprises or consists of feathers. For example, the feathers may be selected from the group consisting of vaned feathers, down feathers, pennaceous feathers, contour feathers, filoplume, remiges and flight feathers.

In one embodiment of the present disclosure, the feathers are vaned feathers or down feathers.

In one embodiment of the present disclosure, the feathers are from poultry. Preferably, the feathers are from chicken and/or turkey. Different types of feathers are characterized by different amino acid content. For example, turkey feathers are richer in cysteine and cysteine, glycine, phenylalanine, proline and tyrosine compared to chicken feathers. Chicken feathers are instead richer in lysine and methionine compared to turkey feathers.

In one embodiment, the process according to the present disclosure further comprises a step of mechanical treatment, wherein the solid parts of the feather material are mechanically treated to be reduced in size. For example the mechanical treatment may comprise or consists of wet milling.

It is not required to fragment the feather material; however, depending on the size of the fermenting reactor, it might be beneficial to have the feather material in small fragments.

Hence, in one embodiment, the process according to the present disclosure further comprises a step of mechanical treatment, and said mechanical treatment is conducted in an apparatus comprising a chopper pump, one or more rotating knives, and/or one or more shredding knives. Said optionally step of mechanical treatment may be conducted prior to the fermenting step.

Fermentation

In order to convert feather material to keratin-rich microfibers as disclosed herein, a fermentation step is required. Said fermentation step comprises hydrolysis of the feather material by a keratin-degrading microorganism, preferably by a keratin-degrading bacteria.

Hence, in one embodiment the fermenting step comprises fermentation of the feather material by a keratin-degrading microorganism. In one embodiment of the present disclosure, the keratin-degrading microorganism or a bacterium is a *Bacillus*. For example, the keratin-degrading microorganism or bacteria may be *Bacillus pumilus*. A *bacillus* strain suitable for conducting hydrolysis of feather material according to the present disclosure is *Bacillus pumilus* FH9, deposited with the Deutsche Sammlung von Microorganismen and Zellkulturen GmbH under deposition number DSM 28594 on 24 Mar. 2014.

The cellular features of *Bacillus pumilus* are synonymous with other species of the genus *Bacillus* including *B. subtilis*, *B. megaterium*, *B. licheniformis*, and *B. cereus*. Therefore, the fermenting step may be performed with these bacterial cells.

In one embodiment, the fermenting step in the process according to the present disclosure is aerobic. The temperature of the fermenting step is between 30° C. and 42° C., such as between 32° C. and 38° C., such as between 34° C. and 38° C., such as between 36° C. and 38° C., such as 37° C. In one embodiment, the temperature of the fermenting step is about 37° C.

The pH of the fermenting step in the process according to the present disclosure is between pH 5 to pH 8, such as between pH 6 to pH 9, such as between pH 6.5 to pH 8.5, such as pH 8. In one embodiment, the pH of the fermenting step is pH 8.

The time for fermentation according to the process of the present disclosure is 12 h to 96 h, such as 12 h to 84 h, such as 24 h to 84 h, such as 36 h to 84 h, such as 48 h to 72 h, such as 24 h. In one embodiment, the time for fermentation is 24 h.

The fermentation conditions and medium composition disclosed herein are optimized for conversion of the feather material into keratin-rich microfibers and give a high yield of microfibers. Changing these conditions may result in different yields of microfibers and also different yields of protein hydrolysate.

In one embodiment the fermenting step comprises mechanical stirring. For example, the fermenting step may be conducted in a stirred-tank fermenter. Such mechanical stirring may contribute to breaking the feather material and so facilitating bacterial hydrolysis.

In one embodiment the fermenting step comprises addition of a pre-culture of the keratin-degrading microorganisms or bacteria. Said pre-culture may come from a seed culture reactor.

In one embodiment, the process according to the present disclosure further comprises a sterilization step and/or a heating step. For example, the sterilization and/or heating step is conducted on the feather material before the fermenting step. In this way, any potentially pathogenic and/or any other contaminating microorganism is eliminated from the feather material, and the risk of introducing competing microorganisms into the fermenter is reduced or eliminated. This results in a pathogenic-free product and prevents contamination of the fermenting reactor and allows for a more efficient and safe hydrolysis of the feather material.

Further Process Steps

The process disclosed herein may further comprise additional optional steps.

In one embodiment, the process according to the present disclosure further comprises a sterilization and/or heating step conducted on the microfibers and/or the protein hydrolysate after the fermenting step. This is only necessary if the microfibers and/or the protein hydrolysate are to be used in applications that require sterile materials, such as cosmetic, pharmaceutical and food industry, amongst other.

When present, the sterilization may be conducted by autoclaving, pasteurization, pascalization, ionizing radiation, UV radiation or antibiotic treatment. Care should be taken not to use conditions that are damaging from proteins and amino acids.

In one embodiment, the process according to the present disclosure comprises:
 a. Providing feather material;
 b. Contacting the feather material with a fermentation medium and keratin-degrading bacteria;
 c. Fermenting the feather material to obtain a composition comprising microfibers and a protein hydrolysate;
 d. Separating the composition in step c) into a supernatant fraction and a precipitate fraction, wherein the precipitate fraction comprises crude microfibers, and
 e. Optionally purifying the precipitate fraction to obtain purified microfibers.

When present, step d. of the process disclosed herein above comprises separating the precipitate fraction into purified microfibers and a supernatant.

In one embodiment, the supernatant fraction obtained in the process described herein and in particular resulting from step c. and/or step d. comprises fermenting cells and may be recirculated to the fermenting step.

In one embodiment, the supernatant fraction obtained in the process described herein and in particular resulting from step c. may be further processed into a fertilizer. Alternatively, the supernatant fraction obtained in the process described herein and in particular resulting from step c. may be further processed into a feed product.

A further aspect of the present disclosure is directed to a process for production of a protein hydrolysate, wherein the process comprises
 a. Providing feather material; and
 b. Fermenting the feather material to obtain a composition comprising a protein hydrolysate.

As described herein above, the process of the present disclosure comprises converting feather material into keratin-rich microfibers and, as a side product, a protein hydrolysate is obtained. Said protein hydrolysate may be a valuable product and its further processing and possible applications are described herein.

In particular, the obtained protein hydrolysate may have a protein content of at least 75% protein by weight, such as of at least 80% protein by weight, such as of at least 85% protein by weight.

Moreover, the obtained protein hydrolysate may have comprise at least 15 different amino acids, such as at least 16 different amino acids, such as at least 17 different amino acids, such as at least 18 different amino acids, such as at least 19 different amino acids, such as about 20 different amino acids. Hence, it is valuable to recover said protein hydrolysate.

System for Extraction of Microfibers

A further aspect of the present disclosure is directed to a system for extraction of microfibers from feather material, comprising a fermenting reactor, said system arranged for performing the process of production of microfibers disclosed herein.

In one embodiment, the system of the present disclosure optionally comprises an apparatus for mechanical treatment, arranged before the fermenting reactor. Various apparatus for mechanical treatment may be used, as described in the section above "Feather material".

In one embodiment, the system of the present disclosure comprises a fermenting reactor arranged for fermenting the feather material to obtain microfibers. Said fermenting reactor can for example be a reactor having mechanical stirring, such as a stirred-tank reactor.

In one embodiment, the system of the present disclosure comprises a fermenting reactor, wherein the fermenting the feather material is performed by keratin degrading microorganism or bacteria.

In one embodiment, the system of the present disclosure further comprises a pre-cultivation reactor arranged for pre-cultivation of the keratin degrading microorganism or bacteria. Said pre-cultivation reactor or seed culture reactor is conveniently connected to the fermenter so that the keratin degrading microorganism or bacteria is transferred from the pre-cultivation reactor to the fermenter. So, in some embodiments the pre-cultivation reactor is coupled to the fermenting reactor to provide the keratin degrading microorganism or bacteria.

In one embodiment, the system of the present disclosure further comprises separation means configured to separate the soluble part of the obtained fermented composition from the insoluble part. The soluble part or supernatant may comprise a protein hydrolysate and fermenting cells. The insoluble part or precipitate comprises crude microfibers. In one embodiment, said separation means comprise one or more centrifuge and/or one or more filtration means. Said separation means have been described herein for example in the section "Hydrolysis of the feather material".

In one embodiment, the system of the present disclosure further comprises one or more purification means configured to purified microfibers from the insoluble part of the fermented composition.

In one embodiment, the system of the present disclosure further comprises one or more purification means wherein the purification means comprise (i) a reactor configured for washing and mixing the insoluble part of the fermented composition, and (ii) additional separation means configured to separate the fermenting cells from the insoluble part of the fermented composition, after the insoluble part of the fermented composition has been mixed and washed. Said purification means have been further described herein for example in the section "Hydrolysis of the feather material".

In one embodiment, the system of the present disclosure further comprises one or more circulation means, such as a pump, configured for passing fluid in a forward flow between the sections of the system.

In one embodiment, the system of the present disclosure further comprises one or more circulation means, may be a pump, and may be configured for passing fluid in a backward flow from one or more of the separation means to the pre-cultivation reactor and/or to the fermenting reactor. Hence, the system of the present disclosure may also comprise connection means connecting the separation means to the fermenter and/or to the pre-cultivation reactor. The system of the present disclosure may also comprise connection means connecting the purification means to the fermenter and/or to the pre-cultivation reactor.

In one embodiment, the system of the present disclosure further comprises a fan, a dryer and/or a cyclone, configured to remove water from the obtained fermented composition and/or from the insoluble part separated from the obtained fermented composition. The benefits of a drying step are further described in the section above "Hydrolysis of the feather material". For example, the dryer may be a spray dryer, a box dryer or a freeze dryer.

In one embodiment, the system of the present disclosure further comprises one or more sterilization reactors configured to perform sterilization. For example the sterilization reactor may be arranged to sterilize the feather material prior to adding said feather material to the fermenter.

In one embodiment, the present disclosure relates to a system comprising:
a. a fermenting reactor, arranged for hydrolysing feather material, connected to
b. separation means, arranged for separating a supernatant fraction from a precipitate fraction, connected to the fermenting reactor by means for re-circulation of the supernatant fraction from the separation means to the fermenting reactor, wherein said precipitate fraction comprises crude microfibers,
c. optionally purification means, arranged for purifying the precipitate fraction, wherein said purification means separate the precipitate fraction into a composition comprising microfibers and a composition comprising fermenting cells, and wherein said purification means are optionally connected to the fermenting reactor by means for re-circulation of the fermenting cells from the purification means to the fermenting reactor,
d. a dryer, arranged for drying of the precipitate fraction and/or of the composition comprising microfibers.

Kit for Extracting Microfibers

A further aspect of the present disclosure relates to a kit of parts for extracting microfibers, comprising a bacterial strain *Bacillus pumilus* FH9, and instructions for use.

In some embodiments, the kit of parts of the present disclosure further comprises salts, such as medium components which are suitable for cultivation of the bacterial strain *Bacillus pumilus* FH9. For example, the kit of parts of the present disclosure may comprise medium components which are suitable for cultivation of the bacterial strain *Bacillus pumilus* FH9, while being free from carbon and/or nitrogen sources.

The instructions may comprise a description of the process for production of microfibers disclosed herein and/or a description of the system for extraction of microfibers from feather material as disclosed herein.

The bacterial strain *Bacillus pumilus* FH9 is described in detailed in the section "Fermentation".

Uses of the Obtained Compositions

In one other aspect, the present disclosure relates to a use of the microfiber composition disclosed herein, and/or obtainable by the process disclosed herein, for manufacture of a composite material.

For example the composition comprising keratin-rich microfibers may be used for production of a wood-based composite material. The composition comprising keratin-rich microfibers may also be used for production of a plastic-based composite material, for example by blending the keratin-rich microfibers with a polymer commonly used for production of plastics. The composition comprising keratin-rich microfibers may also be used for production of a homocomposite, such as a material comprising mostly keratin-rich microfibers.

A further aspect of the present disclosure relates to a use of the composition comprising a protein hydrolysate as disclosed herein as a feed product. The composition comprising a protein hydrolysate may also be used for production of a plant or soil fertilizer. It is worth noticing that, if the composition comprising a protein hydrolysate is to be used for production of a fertilizer, it may be beneficial that the composition also comprises fermenting cells, which may contribute to the fertilizing effect.

The keratin microfibers of the present disclosure, and obtained by the process of the present disclosure are characterized by having low density, low weight, and great sound insulation properties, thanks to their specific size and their three-dimensional structure characterized by the presence of hollow cylindrical structures typical of feathers.

Items

1. A microfiber composition comprising keratin microfibers, wherein said keratin microfibers comprise at least 75% dry weight keratin, and wherein said keratin microfibers have a length of between 20 µm and 200 µm and a diameter of between 1 µm and 10 µm, and wherein said keratin microfibers comprise hollow cylindrical structures.

2. The keratin microfiber composition according to item 1, wherein said keratin microfibers comprise between 75% dry weight keratin and 100% dry weight keratin, such as between 80% dry weight keratin and 100% dry weight keratin, such as between 85% dry weight keratin and 100% dry weight keratin, such as between 75% dry weight keratin and 95% dry weight keratin, such as between 80% dry weight keratin and 95% dry weight keratin, such as between 85% dry weight keratin and 95% dry weight keratin.

3. The keratin microfiber composition according to any one of the preceding items, wherein said keratin microfibers have a length of between 25 µm and 200 µm, such as of between 30 µm and 200 µm, such as of between 35 µm and 200 µm, such as of between 40 µm and 200 µm, such as of between 50 µm and 200 µm, such as of between 60 µm and 200 µm, such as of between 70 µm and 200 µm, such as of between 80 µm and 200 µm, such as of between 90 µm and 200 µm, such as of between 100 µm and 200 µm, such as of between 20 µm and 180 µm, such as of between 20 µm and 150 µm, such as of between 20 µm and 120 µm, such as of between 20 µm and 100 µm, such as of between 20 µm and 90 µm, such as of between 20 µm and 80 µm, such as of between 20 µm and 70 µm, such as of between 20 µm and 60 µm, such as of between 30 µm and 150 µm.

4. The keratin microfiber composition according to any one of the preceding items, wherein said keratin microfibers have a diameter of between 1 µm and 6 µm, such as of between 2 µm and 6 µm, such as of between 3 µm and 6 µm, such as of between 4 µm and 6 µm, such as of between 5 µm and 6 µm, such as of between 1 µm and 5 µm, such as of between 1 µm and 4 µm, such as of between 1 µm and 3 µm, such as of between 1 µm and 2 µm.

5. The keratin microfiber composition according to any one of the preceding items, wherein each keratin microfiber comprises at least one internode and at the most seven internodes, such as at least one internode and at the most six internodes, such as at least one internode and at the most five internodes.

6. The keratin microfiber composition according to any one of the preceding items, wherein said keratin microfibers comprise between 75% dry weight proteins and 100% dry weight proteins, such as between 80% dry weight proteins and 100% dry weight proteins, such as between 85% dry weight proteins and 100% dry weight proteins, such as between 75% dry weight proteins and 90% dry weight proteins.

7. The keratin microfiber composition according to any one of the preceding items, wherein said keratin microfibers comprise between 0.1% dry weight lipids and 2% dry weight lipids, such as about 1% dry weight lipids.

8. A process for production of keratin microfibers from feather material, the process comprising:
    a) Providing a fermentation medium;
    b) Providing feather material at a concentration of at least 25 grams dry weight/L of fermentation medium;
    c) Providing a keratin-degrading bacteria;
    d) Contacting the fermentation medium, the feather material and the keratin-degrading bacteria, and thereby fermenting the feather material to obtain a fermented composition;
    e) Separating the fermented composition obtained in step d) into one supernatant fraction and one precipitate fraction, wherein the precipitate fraction obtained in the separation step comprises keratin microfibers, thereby obtaining keratin microfibers, wherein said keratin microfibers comprise at least 75% dry weight keratin, and wherein said microfibers have a length of between 20 µm and 200 µm.

9. The process according item 8, wherein the separation step comprises centrifugation and/or filtration.

10. The process according to any one of items 8 to 9, wherein the separation step is conducted after the fermenting step.

11. The process according to any one of items 8 to 10, wherein the separation step results in one supernatant fraction and one precipitate fraction.

12. The process according to any one of items 8 to 11, wherein the precipitate fraction obtained in the separation step comprises microfibers, such as crude microfibers.

13. The process according to any one of items 8 to 12, wherein the precipitate fraction obtained in the separation step further comprises fermenting cells.

14. The process according to any one of items 8 to 13, wherein the process further comprises a step of purifying the precipitate fraction.

15. The process according to any one of items 8 to 14, wherein the purification step comprises re-suspending the precipitate fraction.

16. The process according to any one of items 8 to 15, wherein the purification step comprises washing the precipitate fraction and/or mixing the precipitate fraction with water.

17. The process according to any one of items 8 to 16, wherein the purification step comprises centrifugation and/or filtration of the re-suspended, washed and/or mixed precipitate fraction.

18. The process according to any one of items 8 to 17, wherein the purification step results in one supernatant fraction and one precipitate fraction.

19. The process according to any one of items 8 to 18, wherein the precipitate fraction obtained in the purification step comprises purified microfibers.

20. The process according to any one of items 8 to 19, wherein the supernatant fraction obtained in the purification step comprises fermenting cells.

21. The process according to any one of items 8 to 20, wherein the purification step is optionally repeated on the precipitate fraction at least twice, such as at least three times.

22. The process according to any one of items 8 to 21, wherein the process further comprises a step of drying the precipitate fraction obtained from the separation step and/or from the purification step.

23. The process according to any one of items 8 to 22, wherein the microfibers are keratin microfibers.

24. The process according to any one of items 8 to 23, wherein the supernatant fraction obtained in the separation step comprises a protein hydrolysate.
25. The process according to any one of items 8 to 24, further comprising a step of processing the obtained protein hydrolysate into a feed product.
26. The process according to any one of items 8 to 25, wherein the protein hydrolysate comprises soluble proteins, amino acids and/or oligopeptides.
27. The process according to any one of items 8 to 26, wherein the feather material comprises or consists of feathers.
28. The process according to any one of items 8 to 27, wherein the feathers are selected from the group consisting of vaned feathers, down feathers, pennaceous feathers, contour feathers, filoplume, remiges and flight feathers.
29. The process according to any one of items 8 to 28, wherein the feathers are vaned feathers or down feathers.
30. The process according to any one of items 8 to 29, wherein the feathers are from poultry.
31. The process according to any one of items 8 to 30, wherein the feathers are from chicken and/or turkey.
32. The process according to any one of items 8 to 31, further comprising a step of mechanical treatment, wherein the solid parts of the feather material are mechanically treated to be reduced in size.
33. The process according to item 8 to 32, wherein the mechanical treatment comprises wet milling.
34. The process according to any one of items 8 to 33, wherein the mechanical treatment is conducted in an apparatus comprising a chopper pump, one or more rotating knives, and/or one or more shredding knives.
35. The process according to any one of items 8 to 34, wherein the mechanical treatment is conducted prior to the fermenting step.
36. The process according to any one of items 8 to 35, wherein the keratin-degrading bacteria is a *Bacillus*.
37. The process according to any one of items 8 to 36, wherein the keratin-degrading bacteria is *Bacillus pumilus*.
38. The process according to any one of items 8 to 37, wherein the keratin-degrading bacteria is *Bacillus pumilus* FH9, deposited with the Deutsche Sammlung von Microorganismen and Zellkulturen GmbH on 24 Mar. 2014 under deposition number DSM 28594.
39. The process according to any one of items 8 to 38, wherein the fermenting step is aerobic.
40. The process according to any one of items 8 to 39, wherein the temperature of the fermenting step is between 30° C. and 42° C., such as between 32° C. and 38° C., such as between 34° C. and 38° C., such as between 36° C. and 38° C., such as 37° C.
41. The process according to any one of items 8 to 40, wherein pH of the fermenting step is between pH 5 to pH 8, such as between pH 6 to pH 9, such as between pH 6.5 to pH 8.5, such as pH 8.
42. The process according to any one of items 8 to 41, wherein the time for fermentation is 12 h to 96 h, such as 12 h to 84 h, such as 24 h to 84 h, such as 36 h to 84 h, such as 48 h to 72 h, such as 24 h.
43. The process according to any one of items 8 to 42, wherein the fermenting step comprises mechanical stirring.
44. The process according to any one of items 8 to 43, wherein the fermenting step comprises addition of a pre-culture of the keratin-degrading microorganism.
45. The process according to anyone of items 8 to 44, further comprising a sterilization step.
46. The process according to any one of items 8 to 45, further comprising a heating step.
47. The process according to any one of items 8 to 46, wherein the sterilization and/or heating step is conducted on the feather material before the fermenting step.
48. The process according to any one of items 8 to 47, wherein the sterilization and/or heating step is conducted on the microfibers and/or the protein hydrolysate after the fermenting step.
49. The process according to any one of items 8 to 48, wherein the sterilization is conducted by autoclaving, pasteurization, pascalization, ionizing radiation, UV radiation or antibiotic treatment.
50. The process according to any one of items 8 to 49, the process comprising:
    a. Providing feather material;
    b. Fermenting the feather material to obtain a composition comprising microfibers and a protein hydrolysate;
    c. Separating the composition in step b) into a supernatant fraction and a precipitate fraction, wherein the precipitate fraction comprises crude microfibers, and
    d. Optionally purifying the precipitate fraction to obtain purified microfibers.
51. The process according to any one of items 8 to 50, wherein optional step d. comprises separating the precipitate fraction into purified microfibers and a supernatant.
52. The process according to any one of items 8 to 51, wherein the supernatant fraction of step c. and/or of step d. comprises fermenting cells and is recirculated to the fermenting step.
53. The process according to any one of items 8 to 52, wherein the supernatant fraction of step c. is further processed into a fertilizer.
54. The process according to any one of items 8 to 53, wherein the supernatant fraction of step c. is further processed into a feed product.
55. A process for production of a protein hydrolysate, wherein the process comprises
    a. Providing feather material; and
    b. Fermenting the feather material to obtain a composition comprising a protein hydrolysate.
56. The process for production of a protein hydrolysate according to item 55, wherein said process is according to any one of items 8 to 54.
57. A composition comprising a protein hydrolysate obtainable by the process according to any one of the preceding items.
58. The composition according to item 57, wherein the composition is the obtained supernatant after the fermenting step.
59. A composition comprising microfibers obtainable by the process according to any one of the preceding items.
60. The composition according to item 59, wherein the composition is a microfiber composition and is the obtained precipitate after the fermenting step.
61. The composition according to any one of items 59 to 60, wherein said composition comprises at least 75% dry weight keratin, such as at least 80% dry weight keratin, such as at least 85% dry weight keratin.
62. Use of the composition according to any one of items 57 and 58 as a feed product.
63. Use of the microfiber composition according to any one of items 1 to 7, and/or obtainable by the process according to any one of items 8 to 54, for manufacture of a composite material.

64. The use according to item 63, wherein the microfiber composition is used for manufacture of a homocomposite material.
65. The use according to item 63, wherein the microfiber composition is used for manufacture of a fiber-reinforced plastic.
66. A system for extraction of microfibers from feather material, comprising a fermenting reactor, said system arranged for performing the process of production of microfibers according to any one of the preceding items.
67. The system according to item 66, optionally comprising an apparatus for mechanical treatment, arranged before the fermenting reactor.
68. The system according to any one of items 66 to 67, wherein the fermenting reactor is arranged for fermenting the feather material to obtain microfibers.
69. The system according to any one of items 66 to 68, wherein the fermenting the feather material is performed by a keratin degrading microorganism.
70. The system according to any one of items 66 to 69, further comprising a pre-cultivation reactor arranged for pre-cultivation of the keratin degrading microorganism.
71. The system according to any one of items 66 to 70, wherein pre-cultivation reactor is coupled to the fermenting reactor to provide the keratin degrading microorganism.
72. The system according to any one of items 66 to 71, further comprising separation means configured to separate the soluble part of the obtained fermented composition from the insoluble part.
73. The system according to any one of items 66 to 72, further comprising one or more purification means configured to purified microfibers from the insoluble part of the fermented composition.
74. The system according to any one of items 66 to 73, wherein the purification means comprise (i) a reactor configured for washing and mixing the insoluble part of the fermented composition, and (ii) additional separation means configured to separate the fermenting cells from the insoluble part of the fermented composition, after the insoluble part of the fermented composition has been mixed and washed.
75. The system according to any one of items 66 to 74, wherein said separation means comprise one or more centrifuge and/or one or more filtration means.
76. The system according to any one of items 66 to 75, further comprising one or more circulation means, such as a pump, configured for passing fluid in a forward flow between the sections of the system.
77. The system according to any one of items 66 to 76, further comprising one or more circulation means, such as a pump, configured for passing fluid in a backward flow from one or more of the separation means to the pre-cultivation reactor and/or to the fermenting reactor.
78. The system according to any one of items 66 to 77, further comprising a fan, a dryer and/or a cyclone, configured to remove water from the obtained fermented composition and/or from the insoluble part separated from the obtained fermented composition.
79. The system according to any one of items 66 to 78, further comprising one or more sterilization reactors configured to perform sterilization.
80. The system according to any one of items 66 to 79, wherein the sterilization reactor is arranged to sterilize the feather material.
81. The system according to any one of items 66 to 80, the system comprising:
    a. A fermenting reactor, arranged for hydrolysing feather material, connected to
    b. Separation means, arranged for separating a supernatant fraction from a precipitate fraction, connected to the fermenting reactor by means for re-circulation of the supernatant fraction from the separation means to the fermenting reactor, wherein said precipitate fraction comprises crude microfibers,
    c. optionally purification means, arranged for purifying the precipitate fraction, wherein said purification means separate the precipitate fraction into a composition comprising microfibers and a composition comprising fermenting cells, and wherein said purification means are optionally connected to the fermenting reactor by means for re-circulation of the fermenting cells from the purification means to the fermenting reactor,
    d. a dryer, arranged for drying of the precipitate fraction and/or of the composition comprising microfibers.
82. The system according to any one of items 66 to 81, wherein the dryer is a spray dryer, a box dryer or a freeze dryer.
83. A kit of parts for extracting microfibers, comprising a bacterial strain *Bacillus pumilus* FH9, and instructions for use.
84. The kit of parts of item 83, wherein said kit of parts further comprises salts suitable for cultivation of *Bacillus pumilus* FH9.

EXAMPLES

Example 1: General Materials and Methods Used

Feather materials: A mixture of feathers from all body parts of chicken or turkey (wings, tail and down) were collected from local poultry processing industries in Skåne, Sweden.

Dry weight determination: Raw wet feathers (chicken or turkey) were cut into 1-3 cm size using scissors and mixed very well before for a better distribution of all feather parts, then dried at 60° C. for 24-48 h.

Microorganisms: The microbial strain used for feather hydrolysis is a Gram positive, aerobic, and wild type bacterium, *Bacillus pumilus* FH9, deposited with the Deutsche Sammlung von Microorganismen and Zellkulturen GmbH under deposition number DSM 28594 on 24 Mar. 2014. *B. pumilus* or any other microorganisms capable of producing keratinases or proteases can be use in the process.

Cultivation media: Inoculum (seed culture) was prepared in basal medium (BM) containing (g/L) 0.5 $NH_4Cl$; 0.5 NaCl; 0.3 $K_2HPO_4$; 0.3 $KH_2PO_4$; 0.1 $MgCl_2.6H_2O$; and 0.1 g/L yeast extract. Culture pH was adjusted to 8:0. BM was supplemented with 10 g/L casein in 250-1000 mL Erlenmeyer flasks and autoclaved at 121° C. for 15 min.

Flasks were inoculated from a glycerol stock (−20°) or a full loop of an overnight grown colonies of strain *Bacillus pumilus* FH9 on nutrient agar plate. Seed culture flask was incubated for 14-18 h at 37° C. (optical density, OD600, 3.2-3.9).

Medium for fermentative hydrolysis: Basal medium with the same composition as seed culture medium was used for growth and hydrolysis of feather in fermentor cultures. Casein, yeast extract and $NH_4Cl$ were replaced with feathers as the sole carbon and nitrogen source.

In the 5-L scale fermentor (B. Braun Biostat B) temperature was controlled using circulating water bath for heating and cooling. In the 3-L fermentor (Applikon Biobundles), temperature was controlled using circulated tap water into cooling finger or electric heating blanket for warming up.

Example 2: Microfibers from Turkey Feather

Fermentative hydrolysis of turkey feathers in 5-L bioreactor scale (Biostat B) 50-gram dry feather per litre (80 h)

Microfibers source was dry turkey feather 150 g cut into 1-3 cm and autoclaved in 3 litres of basal medium. Culture was inoculated with 16-h grown preculture (5% inoculum size). Culture was aerated at 0.85-1.8 L/L/min (0.5-1.0 volume/volume/minute, vvm) and was mixed with continuous stirring at 400-1000 rpm. Culture pH was controlled at 8.0 using 3M NaOH or 3M HCl. Culture temperature was kept at 37° C.

After 80 h, culture (final vol 3 L) was harvested by centrifugation at 6000 rpm, 5554×g for 10 min at 10-24° C. The recovered insoluble product was dried at 60° C. for 24 h and weighed.

Conclusion: Total of 99.76 g dry material (two-third of starting feather material) was recovered which includes microfibers, cells and non-feather impurities. One-third of the feather was converted to water soluble fraction recovered as a clear supernatant. (Table 1)

Example 3: Microfibers from Chicken Feather

Fermentative hydrolysis of chicken feather 3-L bioreactor scale (Biobundles) 60-gram dry feather per litre (50 h).

Chicken feather was supplied to 1.5 L of basal medium equivalent to 90 grams dry weight.

In this example, a second type of poultry feather (chicken) was used as raw substrate for microfibers and soluble protein hydrolysate production. A slightly higher concentration, 60 g/L dry weight was used. Inoculum and hydrolysis culture were controlled at the same conditions as Example 2. Culture was harvested after a shorter hydrolysis time (50 h). Soluble and insoluble fractions were separated by centrifugation at (6000 rpm, 5554×g for 10 min at 10-24° C.).

The recovered insoluble material was further purified by washing in tap water three times with mixing followed by low speed centrifugation (1200 rpm, 222×g for 2 min at 10-24° C.) to precipitate microfibers and hence separate them from bacterial cells which remain in the decanted supernatant. Recovered fibers were dried at 60° C. for 24 h. The dried microfibers represent 36.53% of the starting feather weight.

Conclusion: The dried microfibers represent ca. 37% of the starting feather weight. A relatively large portion of feather was solubilized (ca. 45%) compared to turkey feather in example 2.

Example 4: Optimized Production of Microfibers

Short-time fermentative hydrolysis of turkey feather 5-L bioreactor scale (Biostat B) 60-gram dry feather per litre (24 h)

The cut turkey feather was used at a slightly higher concentration than that used in Example 2. A total of 120 g dry feather was mixed in to 2 litres of basal medium with the same composition. Air was controlled at 0.5-1.0 vvm while culture was mixed by stirring at 400-600 rpm.

The hydrolysis fermentation was run for a significantly shorter time (24 h). The whole culture mixture was harvested by centrifugation (6000 rpm, 5554×g for 10 min at 10-24° C.).

Downstream processing for microfibers purification was done as described in Example 3.

Conclusion: While maintaining similar productivity and recovery, the improved fermentative hydrolysis process in Example 4 achieved feather hydrolysis after a significantly shorter time-period compared to Example 2 with turkey feather with slightly lower concentration (50 g/L dry weight) or chicken feather with similar concentration in Example 3 (60 g/L dry weight).

The simplified downstream processing used in these examples easily separated the water-soluble fraction as high nutrient hydrolysate for feed applications. The crude insoluble fraction represents two third of the original feather weight (66.50%, Example 2). It could be used as low-grade microfibers for material applications, or it could be purified further via simple water washing steps (Example 3 and 4) to produce high-purity keratin microfibers for fine biomaterial applications. A membrane filtration system could help in improving both purity and recovery of microfibers.

Example 5. Complete Hydrolysis of Feather

Fermentative hydrolysis of chicken feather in 3-L bioreactor scale (BioBundle) 20-gram dry feather per litre (73 h). A total of 30 grams dry chicken feather (cut into 1-3 cm) was sterilized in 1.5 L of basal medium comprising yeast extract and ammonium chloride. The culture was inoculated with 16-h grown preculture (5% inoculum size). The culture was aerated at 1.0-2.0 L/L/min (0.67-1.33 volume/volume/minute, vvm) and was mixed with continuous stirring at 400-1000 rpm. The pH of the culture was controlled and kept at 8.0 using 3 M NaOH or 3 M HCl. The culture temperature was kept at 37° C. The fermentation continued until a visible complete hydrolysis was observed, amount to about 73 h. Residuals and non-hydrolyzed feather were then separated by centrifugation at 6000 rpm (5554×g) for 15 min.

Results from Examples 2, 3, 4 and 5 are summarized in Table 1 to give an overview of the different crude and purified product from feather bacterial hydrolysis.

TABLE 1

Production of microfibers and keratin hydrolysate from chicken and turkey feathers via bacterial hydrolysis. (The total % may be over 100 due to presence of salts in the fermentation media, or due to incomplete drying/lyophilization.)

| | | | | Hydrolysate (g/L, % of original substrate) | | | |
|---|---|---|---|---|---|---|---|
| Example | Feather source | Feather concentration (g/L) | Hydrolysis time (h) | Soluble hydro-lysate | Pure fibers | Residual fibers and cells | Residual feather |
| 2 | Turkey | 50.0 | 80 | 14.0 g/L, 28.0% | | 33.3 g/L, 66.5% | 2.3 g/L, 5.5% |
| 3 | Chicken | 60.0 | 50 | 27.2 g/L, 45.3% | 22 g/L 36.7% | 10.1 g/L 16.8% | 0.7 g/L 1.2% |
| 4 | Turkey | 60.0 | 24 | 14.7 g/L, 24.5% | 22 g/L, 36.5% | 17.7 g/L, 29.5% | 5.7 g/L, 10.5% |
| 5 | Chicken | 20.0 | 73 | 19.8 g/L, 98.5% | | 0.9 g/L, 4.3% | |

Conclusion: 1.56 g dry material (4.3% of starting feather material) was observed as residual feather and growing cells. This fermentation succeeded to achieve almost complete hydrolysis of feather at this concentration. The supernatant after dried (lyophilized) recovered almost the protein content in feather substrate used (20.0 g/L) (Table 1). The dry supernatant obtained is a completely water-soluble powder smell like protein concentrate and have a light beige color.

The data in Table 1 indicate that the initial feather concentration is an important factor for directing the bacterial hydrolysis towards production of keratin microfibers (insoluble in water/aqueous conditions) or a soluble protein concentrate. In particular, an initial feather concentration of 25 g dry weight/L, preferably of 50 g dry weight/L or higher, seems to be required for directing the hydrolysis towards production of microfibers.

Example 6: Amino Acids Analysis of Soluble Fraction of Chicken and Turkey Feather Hydrolysates Protein content and amino acid analyses, Dumas and oxidative hydrolysis, respectively, were done at Eurofins Food & Feed Testing Sweden AB, Lidköping, Sweden. Samples from lyophilized soluble hydrolysate from Example 3 and 4 were used for these analyses. The recovered soluble keratin hydrolysate from chicken or turkey feather contains similar protein content as the original protein content in feather—around 87%. The amino acids content from both chicken and turkey feathers can be of high nutritional value for animal feed applications. Interestingly, soluble turkey feather hydrolysate shows higher soluble amino acid contents and high levels of specific amino acids such as cysteine/cystine, glycine and tyrosine, compared to chicken feather hydrolysate, which may increase its value in feed applications.

TABLE 2

Comparison of amino acid profile and concentration in soluble hydrolysates from chicken and turkey feathers.

| Amino Acid | Soluble turkey feather hydrolysate (% weight) | Soluble chicken feather hydrolysate (% weight) |
|---|---|---|
| Alanine | 1.26 | 1.32 |
| Arginine | 2.99 | 2.59 |
| Aspartic Acid | 4.95 | 4.09 |
| Cystein + Cystine | 7.12 | 3.35 |
| Glutamic Acid | 4.13 | 4.44 |
| Glycine | 5.63 | 1.97 |
| Histidine | 0.53 | 0.73 |
| Hydroxyproline | 0.05 | 0.05 |
| Isoleucine | 0.69 | 0.85 |
| Leucine | 1.81 | 1.91 |
| Lysine | 0.83 | 1.07 |
| Methionine | 0.22 | 0.34 |
| Omitine | 0.09 | 0.01 |
| Phenylalanine | 6.86 | 4.66 |
| Proline | 4.82 | 3.58 |
| Serine | 3.38 | 3.38 |
| Threonine | 1.10 | 1.35 |
| Tyrosine | 3.63 | 0.02 |
| Valine | 1.75 | 1.71 |
| Total Amino Acid % | 51.78 | 37.42 |
| Protein content % by weight | 86.9 | 84.7 |

Example 7: Characterization of Keratin-Rich Microfibers from Feathers

FIG. 1 explains the physical structure of birds' feather.

Figure 3:
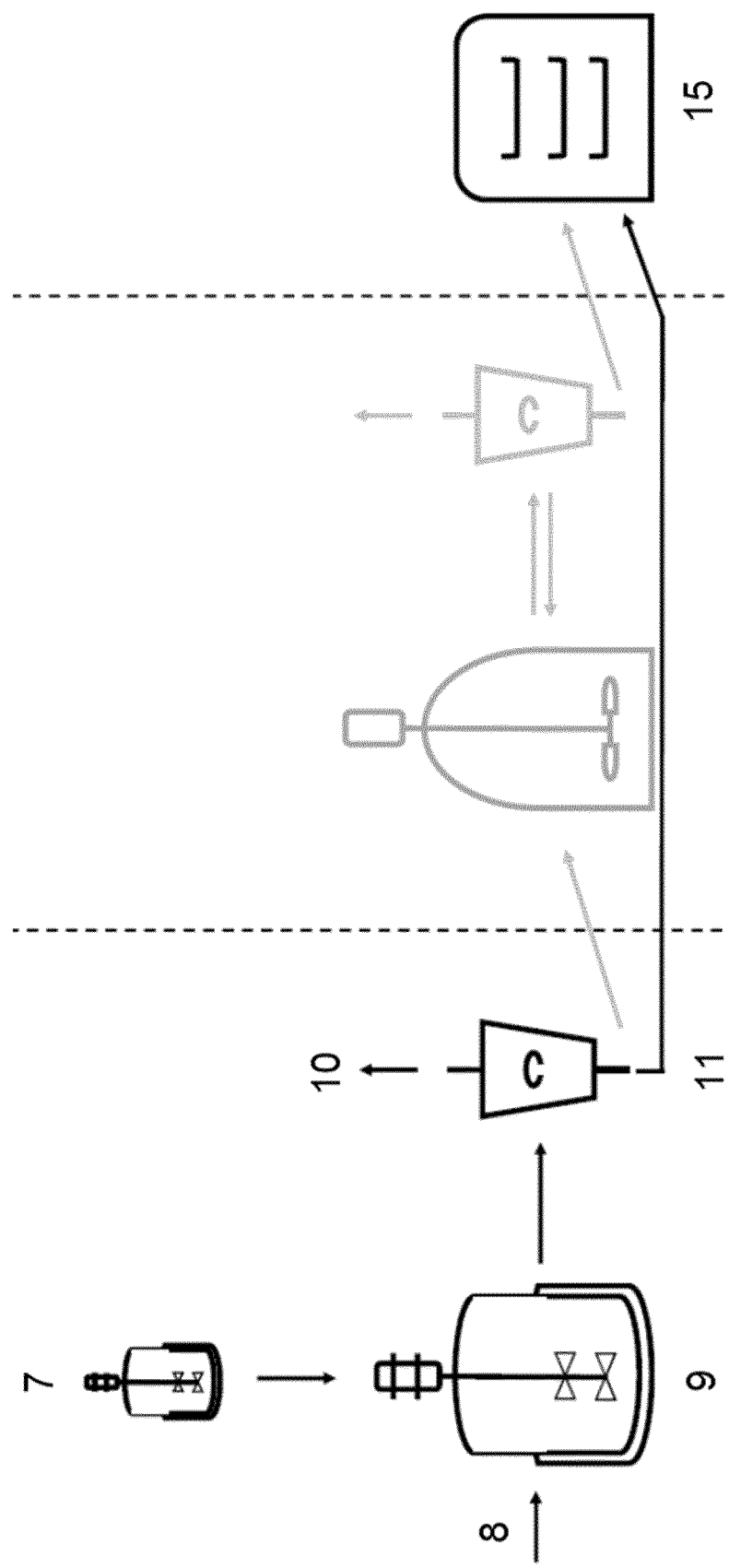
FIG. 3: Flow diagram of feather hydrolysis process for obtaining crude microfibers, including cell recycling:
A) Seed culture grown for 12-18 h in basal medium
B) Feather fermentative hydrolysis 24-80 h (24 h). Dry feather concentration of 50-60 g/L
C) Separation of soluble keratin hydrolysate at low speed centrifugation or microfiltration
D) Recovery of cells and their use as inoculum for next hydrolysis batches or as plant/soil fertilizer
E) Drying of recovered crude microfibers.
Legend: 7: seed culture; 8: wet feather; 9: hydrolysis; 10: soluble hydrolysate; 11: crude microfibers; 15: drying.

The insoluble feather hydrolysate represents the main portion of recovered hydrolysate from both chicken and turkey feathers, almost half or two-third of recovered hydrolysates (Table 1). Recovered keratin fibers from feather represent the smallest fibrous building blocks of the native feather physical structure (FIG. 3B). The bacterial hydrolysis process partially degrades feather barbs and barbules into hollow-cylindrical microfibers of 1-5 internodes. The length of these fibers is in the range of 30-150 µm and width of 2-6 µm. These micro-scale fibers being keratin-based and with hollow cylindrical structures, will have a broader scope of applications in both material industry and biomedicine. (Reddy, 2015)

Figure 4:
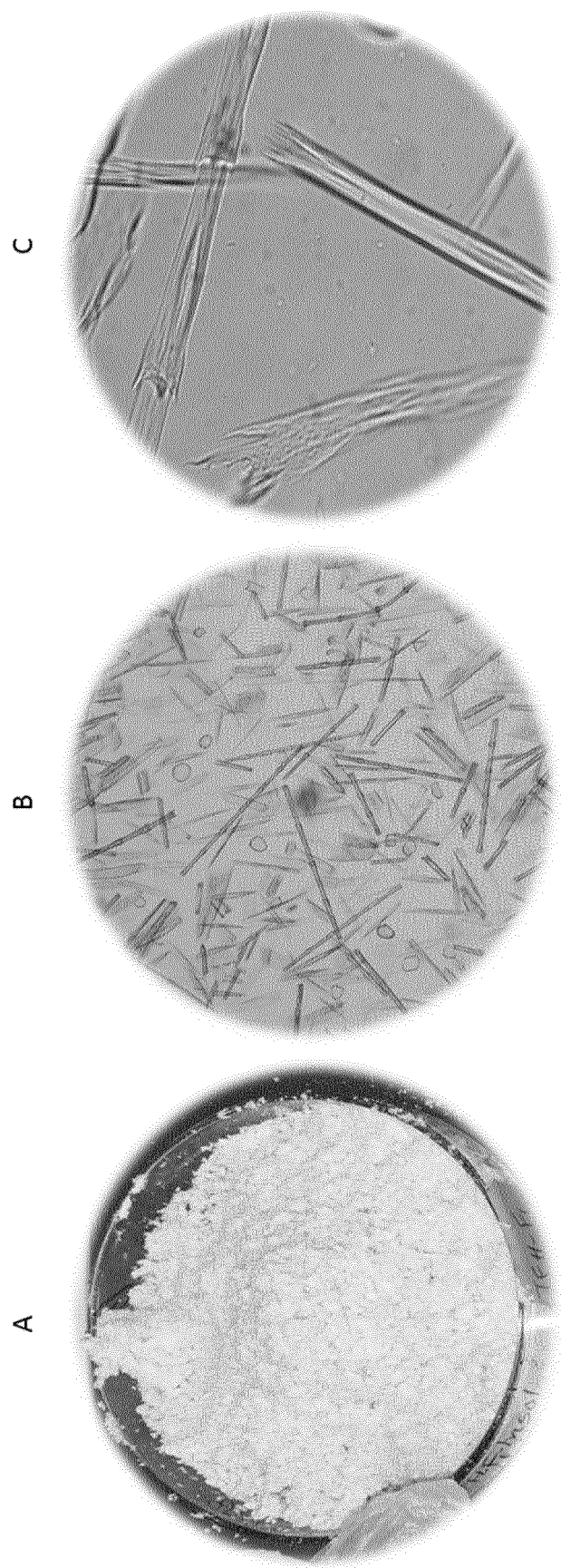
FIG. 4: Microfibers from poultry feathers: A) recovered microfibers in the form of dry powder, B) Microscopic graph of microfibers, C) Microscopic graph of microfibers at higher magnification (100× lens).

The purified insoluble fraction was dried at 60° C. for 24 h. Keratin microfibers in the form of very fine powders were recovered after drying as represented in FIG. 4A.

Example 8: Composite Formation

Figure 5:
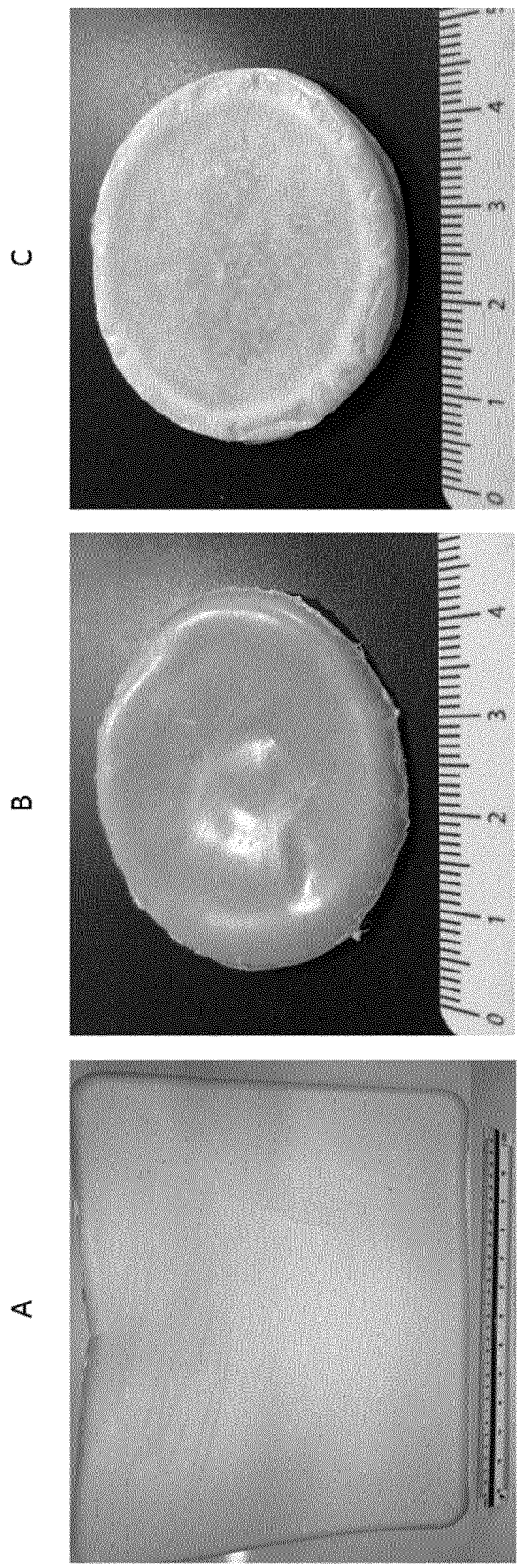
FIG. 5: Microfibers composite casting: A) Homo-composite made by direct casting of recovered microfibers and drying at 60° C. for 24 h; B) PHA-microfibers composites (9:1), dried at room temperature; C) Capa-microfibers composite (9:1), dried at room temperature.

To check the composite reinforcement applicability of the fibrous hydrolysate, the recovered crude microfibers were used to make composites with biodegradable polymers by simple casting and drying:
A) Feather homocomposites
    The recovered wet feather hydrolysate microfibers from Example 4 were casted in plastic tray (tray size: 28×38 cm; layer thickness: 1-3 mm) and dried at 60° C. for 24 h.
    The dried feather microfibers formed a compact keratin fibers composite with similar appearance to wood-based composites. (FIG. 5 A)
B) Feather reinforced bioplastics: Recovered feather microfibers were reinforced by vigorous mixing into solubilized biopolymers (available in lab polyesters, the bioplastic polyhydroxyalkanoate, PHA, and compostable polycaprolactone, Capa, Perstorp, Sweden).
    One portion of dry feather microfibers were reinforced into nine portions of solubilized polyesters, PHA and Capa (0.1 g fibers: 0.9 g polyester). Mixtures were casted in glass plates and dried at room temperature. FIG. 5 B, C. Dried composites at these mixing ratios showed continuous films with similar appearance as the bioplastic material used. This result simply proves the reinforcement applicability of produced microfibers for biocomposites formation.

Example 9: Further Composites

Recovered feather microfibers were reinforced by vigorous mixing into solubilized biopolymers, and then dried overnight 50° C. Compounding was done by mixing the dried polymer with or without dried microfibers at the appropriate melting temperature each polymer for 3 min with Argon gas supply:
100° C. (CABA); 180, 180, 185° C. (PHB)
70 RPM
Argon
3 min
Injection moulding was done by melting the compounded homo- or mixed composites at the ideal melting temperature for each polymer then extruded with pressure at a lower temperature in three steps:
100° C. (Melt, CAPA); 185° C. (Melt, PHB);
40° C. (Mould, CAPA); 90° C. (Mould, PHB);
Step 1:10 bar 2 s
Step 2: 16 bar 10 s
Step 3: 16 bar 15 s
Composites were extruded into two shapes, dog-bone and filament (fibers) forms. Replication, three or four different sample weights of each composites were extruded. ThermoFischer Scientific extruder (Thermo Fisher Process 11 extrusion line) was used. according to the following scheme:

TABLE 3

Keratin microfibers reinforced materials

| Heterocomposite | % (grams) biopolymer | % (grams) keratin microfibers | Weight of final product (replicates separated by semi-columns) |
|---|---|---|---|
| 90% PHB | 90% PHB (6.3 g) | 10% Microfiber (0.7 g) | 6.16 g; 6.17 g; 6.30 g; 6.39 g |
| 80% PHB (FIG. 6C and D) | 80% PHB (5.6 g) | 20% Microfiber (1.4 g) | 5.74 g; 6.18 g; 6.25 g; 6.25 g |
| 90% CAPA (FIG. 6A and B) | 90% CAPA (6.3 g) | 10% Microfiber (0.7 g) | 6.19 g; 6.62 g; 6.35 g; 6.55 g |
| 80% CAPA | 80% CAPA (5.6 g) | 20% Microfiber (1.4 g) | 6.77 g; 6.70 g; 6.62 g |

Figure 6:
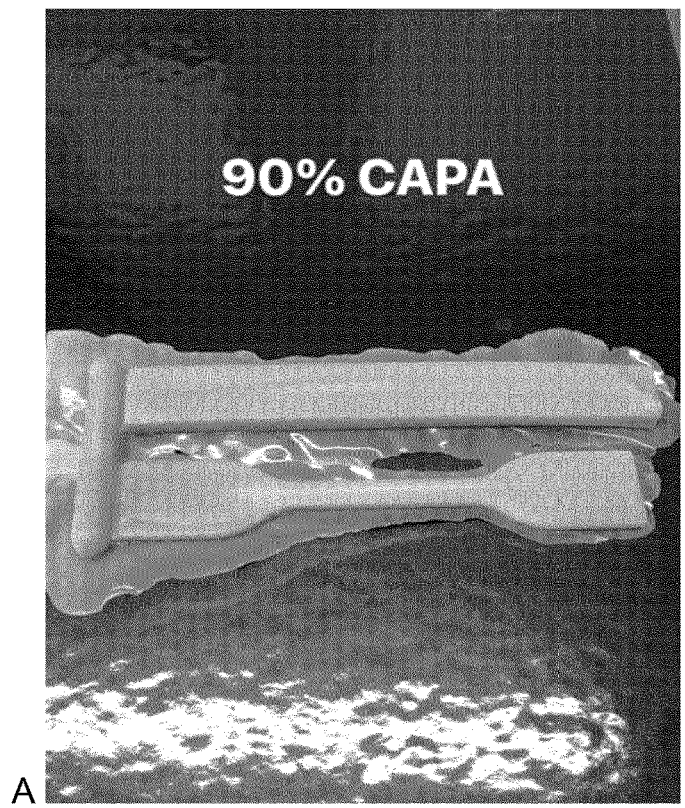
FIG. 6: representative CABA-keratin microfibers (A and B) and PHB-keratin microfibers (C and D materials.
Figure 6:
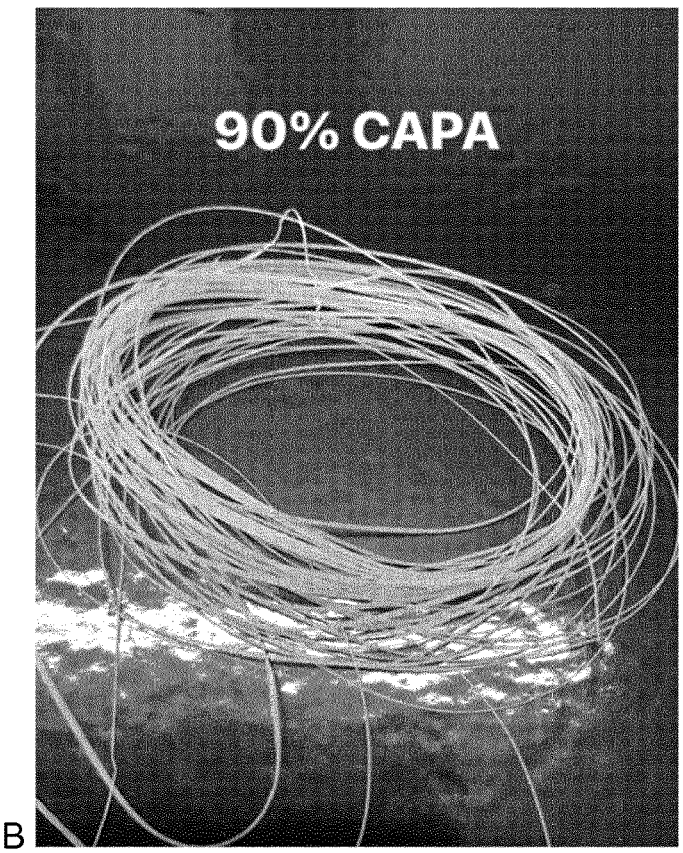
Figure 6:
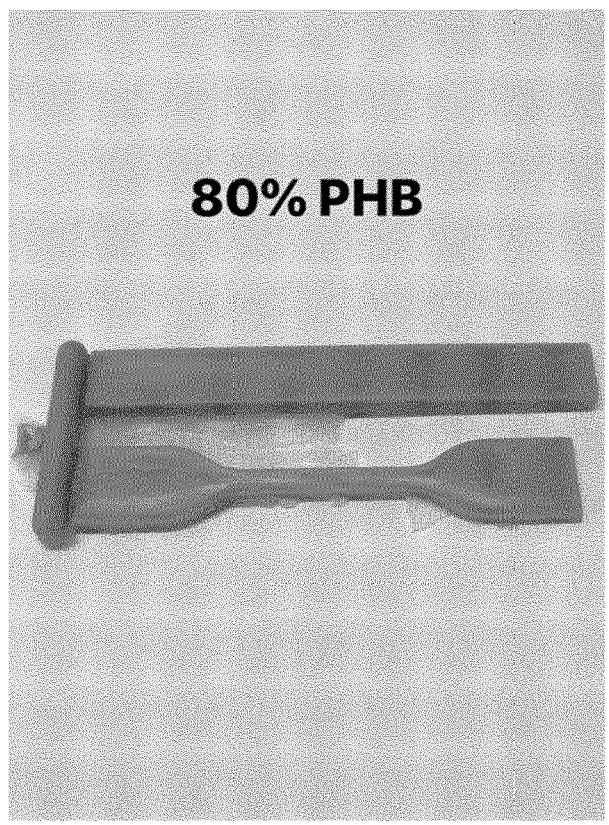
Figure 6:
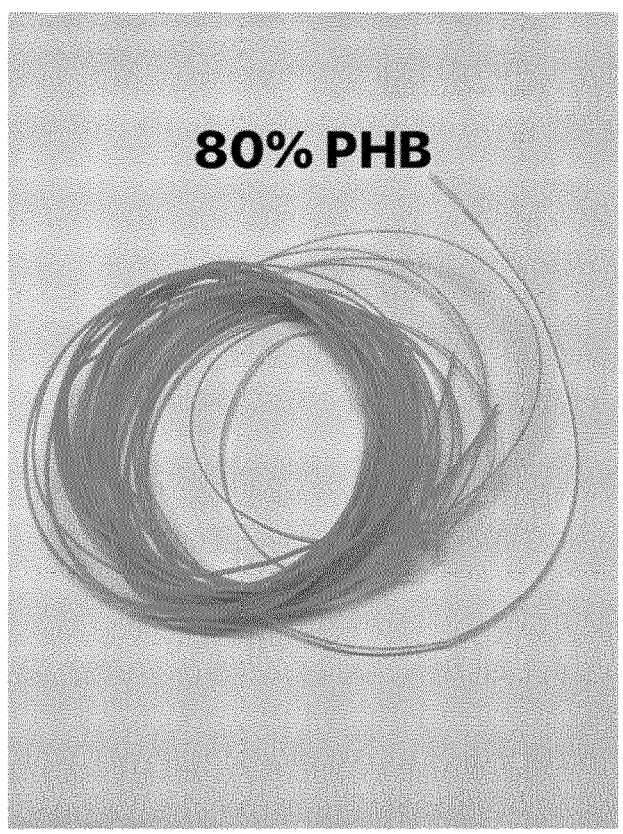

Results are shown in Table 3, "Weight of final product" and FIG. 6. Results for homocomposites not reinforced with keratin microfibers are not shown here.

Example 10. Optimized Purification of Microfibers

1. After microbial hydrolysis 24 h, fibers were filtered throw a mesh 1-5 mm to exclude big parts of feather.
2. Centrifugation at high speed was applied to separate hydrolysate (8000 rpm, 9722×g, for 15 min at 20° C.)
3. Microfibers pellets can be recovered and transferred back to fermenter. Fill with 2-L of autolysis buffer contains (g/L) NaCl, 9.0; $K_2HPO_4$, 0.2; and $KH_2PO_4$, 0.2.
4. Crude microfibers pellets were mixed at 400-600 rpm at controlled pH 7.0 and temperature 37° C. for 2 hours.
5. Cleaned microfibers were harvested via centrifugation at a low speed (1200 rpm, 200×g).
6. Cleaned microfibers were washed 1-3 times with water before drying at 50° C. overnight.
7. Surfactant (dish detergent) can be added during the first water washing step to reduce protein smell, gave whiter color, and prevent aggregation during drying.
Results for keratin microfibers purified according to steps 1-6 are not presented here.

REFERENCES

Aranberri, I., Montes, S., Azcune, I., Rekondo, A., Grande, H. J., 2017. Fully biodegradable biocomposites with high chicken feather content. Polymers (Basel). 9. https://doi.org/10.3390/polym9110593

Büyükkaya, K., 2017. Effects of the Fiber Diameter on Mechanic Properties in Polymethyl-Methacrylate Composites Reinforced with Goose Feather Fiber. Mater. Sci. Appl. 8, 811-827. https://doi.org/10.4236/msa.2017.811059

Graeter, G. III., W. Schmidt, M. J. Line, C. Thomas, Waters, R. M., 1998. Fiber and fiber products produced. U.S. Pat. No. 5,705,030.

Karthikeyan, R., Balaji, S., Sehgal, P. K., 2007. Industrial applications of keratins—A review, Journal of Scientific & Industrial Research. 66, 710-715.

Manginsay, G. P., Guinita-Cabahug, R., 2015. Chicken Feathers as Substitute for Fine Aggregates in Concrete. Mindanao J. Sci. Technol. 13, 109-131.

Meyerhoeffer, C., Showalter, A., n.d. Systems, devices, and/or methods for washing and drying a product. U.S. Pat. No. 8,182,551.

Molins, G., Alvarez, M. D., Garrido, N., Macanás, J., Carrillo, F., 2012. Chicken feathers based composites: A Life Cycle Assessment. 15th Eur. Conf. Compos. Mater. 24-28 Jun. 2012.

Papadopoulos, M. C., 1985. Processed chicken feathers as feedstuff for poultry and swine. A review. Agric. Wastes 14(4), 275-290. https://doi.org/10.1016/50141-4607(85)80009-3

Reddy, N., 2015. Non-food industrial applications of poultry feathers. Waste Manag. 45 91-107. https://doi.org/10.1016/j.wasman.2015.05.023

Sinkiewicz, I., Śliwińska, A., Staroszczyk, H., Kołodziejska, I., 2017. Alternative Methods of Preparation of Soluble Keratin from Chicken Feathers. Waste and Biomass Valorization. 8, 1043-1048. https://doi.org/10.1007/s12649-016-9678-y Stettenheim, P. R., 2000. The Integumentary Morphology of Modern Birds—An Overview. Amer. Zool. 40, 461-477.

Supri, A. G., Aizat, A. E., Yazid, M., Masturina, M., 2015. Chicken feather fibers-recycled high-density polyethylene composites: The effect of ∈-caprolactam. J. Thermoplast. Compos. Mater. 28, 327-339. https://doi.org/10.1177/0892705713484746

Tesfaye, T., Sithole, B., Ramjugernath, D., 2017. Valorisation of chicken feathers: a review on recycling and recovery route—current status and future prospects. Clean Technol. Environ. Policy. 19(10), 2363-2378. https://doi.org/10.1007/s10098-017-1443-9

Wrześniewska-Tosik, K., Marcinkowska, M., Niekraszewicz, A., Potocka, D. A., Mik, T., Pałczyńska, M., 2011. Fibrous composites based on keratin from chicken feathers. Fibres and Text. East. Eur. 19(6), 118-123.

The invention claimed is:

1. A process for production of keratin microfibers from feather material, the process comprising:
   a) Providing a fermentation medium;
   b) Providing feather material at a concentration of at least 25 grams dry weight/L of fermentation medium;
   c) Providing a keratin-degrading bacteria;
   d) Contacting the fermentation medium, the feather material and the keratin-degrading bacteria, and thereby fermenting the feather material to obtain a fermented composition;
   e) Separating the fermented composition obtained in step d) into one supernatant fraction and one precipitate fraction, wherein the precipitate fraction obtained in the separation step comprises keratin microfibers, thereby obtaining keratin microfibers, wherein said keratin microfibers comprise at least 75% dry weight keratin, and wherein said microfibers have a length of between 20 μm and 200 μm and a diameter of between 1 μm and 10 μm, and wherein said keratin microfibers comprise hollow cylindrical structures.

2. The process according to claim 1, wherein the feather material is provided at a concentration of 40 g dry weight/L or above.

3. The process according to claim 1, wherein the feather material is the sole source of carbon and/or nitrogen for the keratin-degrading bacteria.

4. The process according to claim 1, wherein the separating step comprises centrifugation and/or filtration.

5. The process according to claim 1, wherein the process further comprises a step of purifying the precipitate fraction, and wherein the step of purifying comprises:
   re-suspending the precipitate fraction, and/or washing the precipitate fraction and/or mixing the precipitate fraction with water; and
   centrifugation and/or filtration of the re-suspended, washed and/or mixed precipitate fraction.

6. The process according to claim 5, wherein the purification step results in one supernatant fraction and one precipitate fraction, and wherein the precipitate fraction obtained in the purification step comprises purified keratin microfibers, and the supernatant fraction obtained in the purification step comprises fermenting cells.

7. The process according to claim 6, wherein the supernatant fraction obtained in the purification step comprises fermenting cells and is recirculated to the fermenting step.

8. The process according to claim 1, wherein the feather material comprises or consists of feathers.

9. The process according to claim 8, wherein the feathers are from poultry.

10. The process according to claim 1, wherein said keratin-degrading bacteria belongs to the genus *Bacillus*.

11. The process according to claim 1, wherein the keratin-degrading bacteria is selected from the group consisting of *Bacillus pumilus, B. subtilis, B. megaterium, B. licheniformis,* and *B. cereus*.

12. The process according to claim 1, wherein the keratin-degrading bacteria is *Bacillus pumilus*.

13. The process according to claim 1, wherein the keratin-degrading bacteria is *Bacillus pumilus* FH9, deposited with the Deutsche Sammlung von Microorganismen and Zellkulturen GmbH on 24-03-2014 under deposition number DSM 28594.

14. The process according to claim 1, wherein the fermenting step is aerobic.

15. The process according to claim 1, wherein the temperature of the fermenting step is between 30° C. and 42° C., and/or wherein pH of the fermenting step is between pH 5 to pH 8, and/or wherein the time for fermentation is 12 h to 96 h.

16. The process according to claim 1, wherein the fermenting step comprises mechanical stirring.

* * * * *